(12) United States Patent
Sarpong

(10) Patent No.: US 11,166,836 B1
(45) Date of Patent: Nov. 9, 2021

(54) BAG FOR CAPTURING BODILY FLUIDS

(71) Applicant: Cecil Sarpong, Bronx, NY (US)

(72) Inventor: Cecil Sarpong, Bronx, NY (US)

( * ) Notice: Subject to any disclaimer, the term of this patent is extended or adjusted under 35 U.S.C. 154(b) by 211 days.

(21) Appl. No.: 16/351,793

(22) Filed: Mar. 13, 2019

(51) Int. Cl.
*A61F 5/44* (2006.01)
*A61M 25/00* (2006.01)

(52) U.S. Cl.
CPC .......... *A61F 5/4408* (2013.01); *A61F 5/4401* (2013.01); *A61M 25/0017* (2013.01)

(58) Field of Classification Search
CPC ............. A61F 5/44–443; A61F 5/4401; A61F 5/4407; A61F 5/4408; A61F 2005/4402; A61F 2005/4415; A61F 2013/530481; A61F 2013/00748; A61M 1/0001; A61M 1/0017; A61M 1/0019; A61M 25/0017
See application file for complete search history.

(56) References Cited

U.S. PATENT DOCUMENTS

| 8,357,105 | B2 | 1/2013 | Fontaine et al. | |
| 8,663,181 | B2 | 3/2014 | Yang | |
| 2004/0204695 | A1* | 10/2004 | Bisbee | A61F 5/4408 604/349 |
| 2011/0172616 | A1* | 7/2011 | Hartwell | A61M 1/0003 604/319 |
| 2013/0035653 | A1* | 2/2013 | Kannankeril | A61F 5/445 604/333 |
| 2013/0245585 | A1* | 9/2013 | Letellier | A61J 1/10 604/328 |
| 2013/0304004 | A1* | 11/2013 | Riesinger | A61M 1/0017 604/319 |
| 2018/0325720 | A1* | 11/2018 | Brites Pinto | B65D 33/25 |

FOREIGN PATENT DOCUMENTS

| CN | 201171815 Y | * | 12/2008 | |
| KR | 100958041 B1 | * | 5/2010 | |
| KR | 200486331 Y1 | * | 5/2018 | ........... A61F 5/4407 |
| WO | WO-2018075464 A1 | * | 4/2018 | ........ A61M 25/0017 |

* cited by examiner

*Primary Examiner* — Nicholas J Weiss
*Assistant Examiner* — Eric Rassavong
(74) *Attorney, Agent, or Firm* — Sanchelima & Associates, P.A.; Christian Sanchelima; Jesus Sanchelima

(57) ABSTRACT

The present invention relates a bag for capturing bodily fluids. The bag comprises a body, wherein the body is a resealable body having a resealing means configured at one edge thereof, the resealing means include a press fit seal; a capturing means coupled to the body for capturing the bodily fluid and allow the bodily fluid to be collected within the body, wherein the capturing means is a catheter, and the bodily fluid that the catheter captures is urine; an absorbing means disposed within the body to receive the bodily fluid and convert the bodily fluid into a gel, thereby preventing the leakage out of the body, wherein the absorbing means is an absorbent pad, and the absorbent pad is made of super absorbent polymers; and a strap means for making the bag wearable on the human body.

11 Claims, 4 Drawing Sheets

BAG FOR CAPTURING BODILY FLUIDS

BACKGROUND OF THE INVENTION

1. Field of the Invention

The present disclosure relates to the field of bags for capturing bodily fluids, e.g., a urine bag. In particular, the present disclosure relates to a bag for capturing bodily fluids, which prevents the leakage or spillage of the fluid therefrom.

2. Description of the Related Art

Individuals having condition that affects the nerves that control the bladder, such as spina bifida, multiple sclerosis (MS), stroke or spinal injury are required to use catheterized urine bags. The conventional urine bags, however, are prone to accidental leakage or spillage, which might be a cause of embarrassment to the users. This is not desired.

Several designs for urine bags have been designed in the past. None of them, however, are known to have been designed to be reusable, while at the same time, having a configuration that prevents the leakage or spillage of the fluids from the urine bag.

Applicant believes that a related reference corresponds to U.S. Pat. No. 8,663,181 filed by KUO-HUANG YANG. The Yang reference discloses a disposable urine bag device that includes a bag having an open top; and two cuff-like supporting members formed on two sides of the open top of the bag, wherein two fingers are allowed to insert into the supporting members to position the bag and adjust size of the open top of the bag. However, the urine bag disclosed in the Yang reference is not suitable for use to patients who require catheterized urine bags. Furthermore, the configuration of the urine bag disclosed the Yang reference is not designed to prevent accidental spillage.

Applicant believes that another related reference corresponds to U.S. Pat. No. 8,357,105 filed by CHELSEY FONTAINE, STEPHEN TULLY, and LAWRENCE SALVADORI. The Fontaine reference discloses a urine meter for use with a urine collection bag or system. More specifically, the Fontaine reference relates to a urine meter constructed to facilitate faster drainage and more precise volume measurement. However, the urine bag disclosed in the Fontaine reference fails to disclose any feature designed to prevent accidental spillage therefrom.

Other documents describing the closest subject matter provide for a number of more or less complicated features that fail to solve the problem in an efficient and economical way. None of these patents suggest the novel features of the present invention.

SUMMARY OF THE INVENTION

It is an object of the present invention to provide a bag for capturing bodily fluids having a configuration designed to prevent accidental spills or leakage.

It is yet another object of the present invention to provide a bag for capturing bodily fluids having a reusable configuration.

Further objects of the invention will be brought out in the following part of the specification, wherein detailed description is for the purpose of fully disclosing the invention without placing any limitations thereon.

BRIEF DESCRIPTION OF THE DRAWING

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
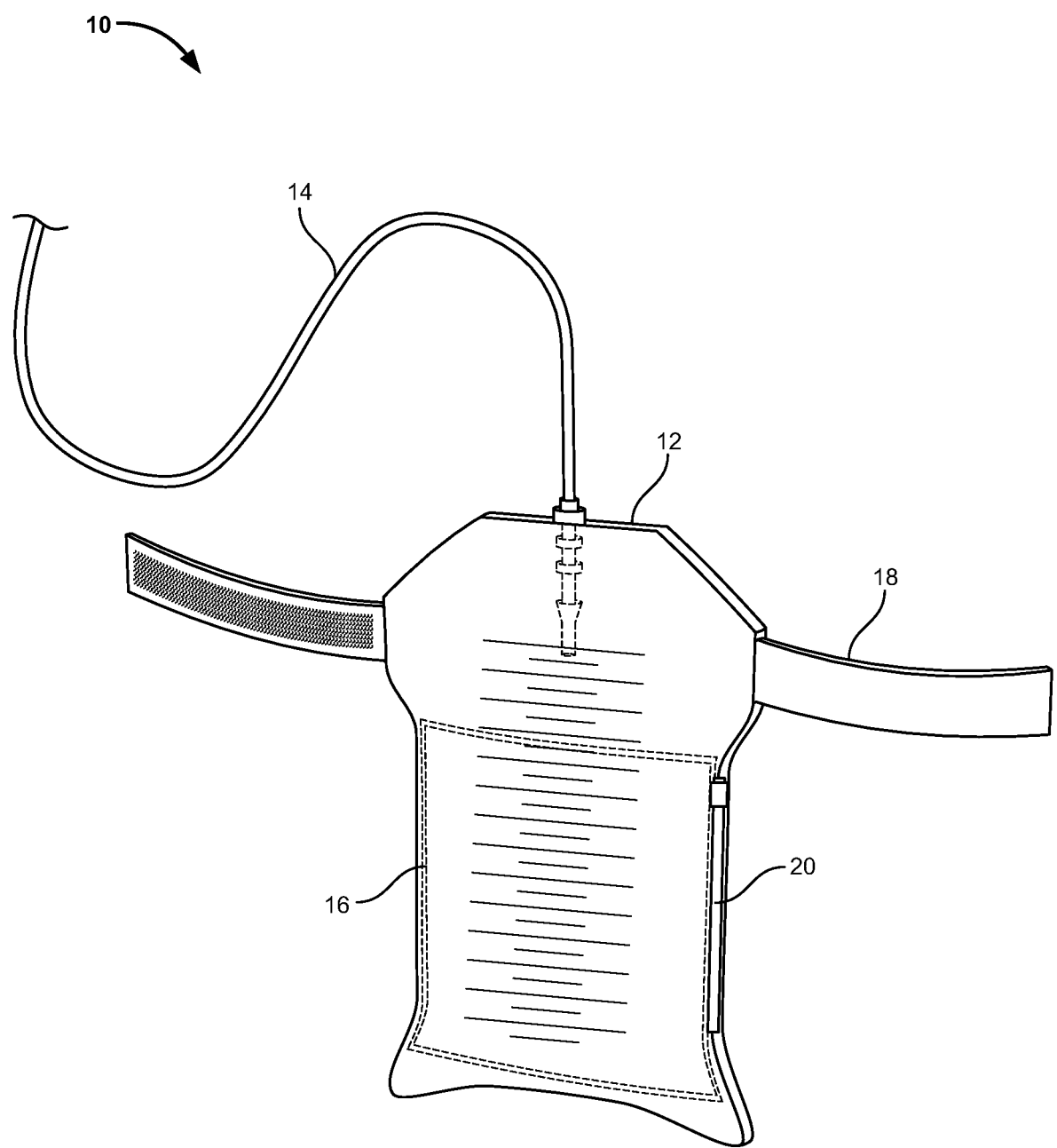
FIG. 1 illustrates an isometric view of a urine bag 10, in accordance with an embodiment of the present invention, wherein the urine bag 10 comprises a body 12, a capturing means 14 extending from the body 12, an absorbing means 16 disposed within the body 12, and a strap means 18 provided on the body 12 for allowing the urine bag 10 to be worn by the user.
Figure 2:
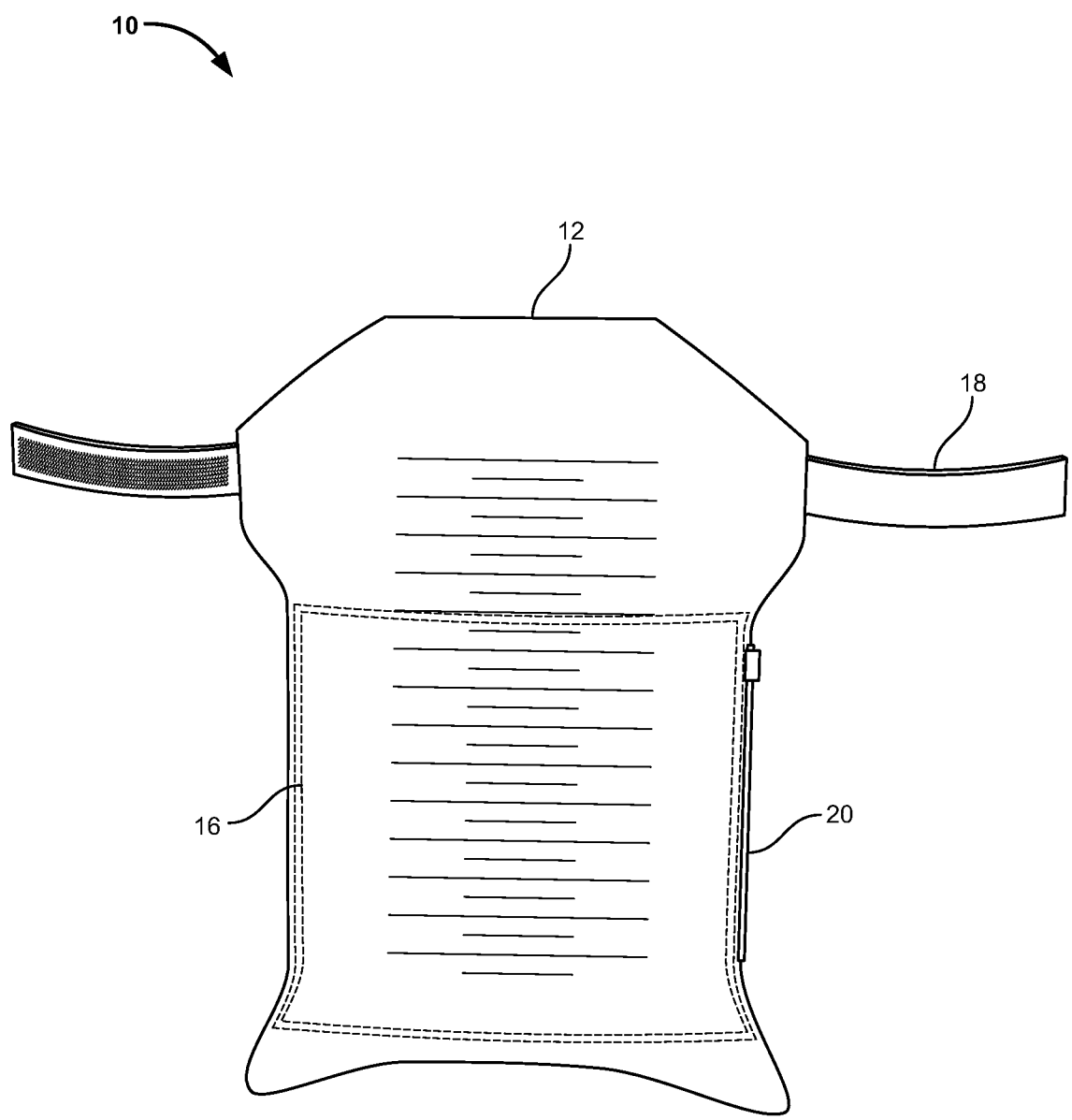
FIG. 2 illustrates a front view of the urine bag 10, in accordance with an embodiment of the present invention, having a measurement scale configured thereon.
Figure 3:
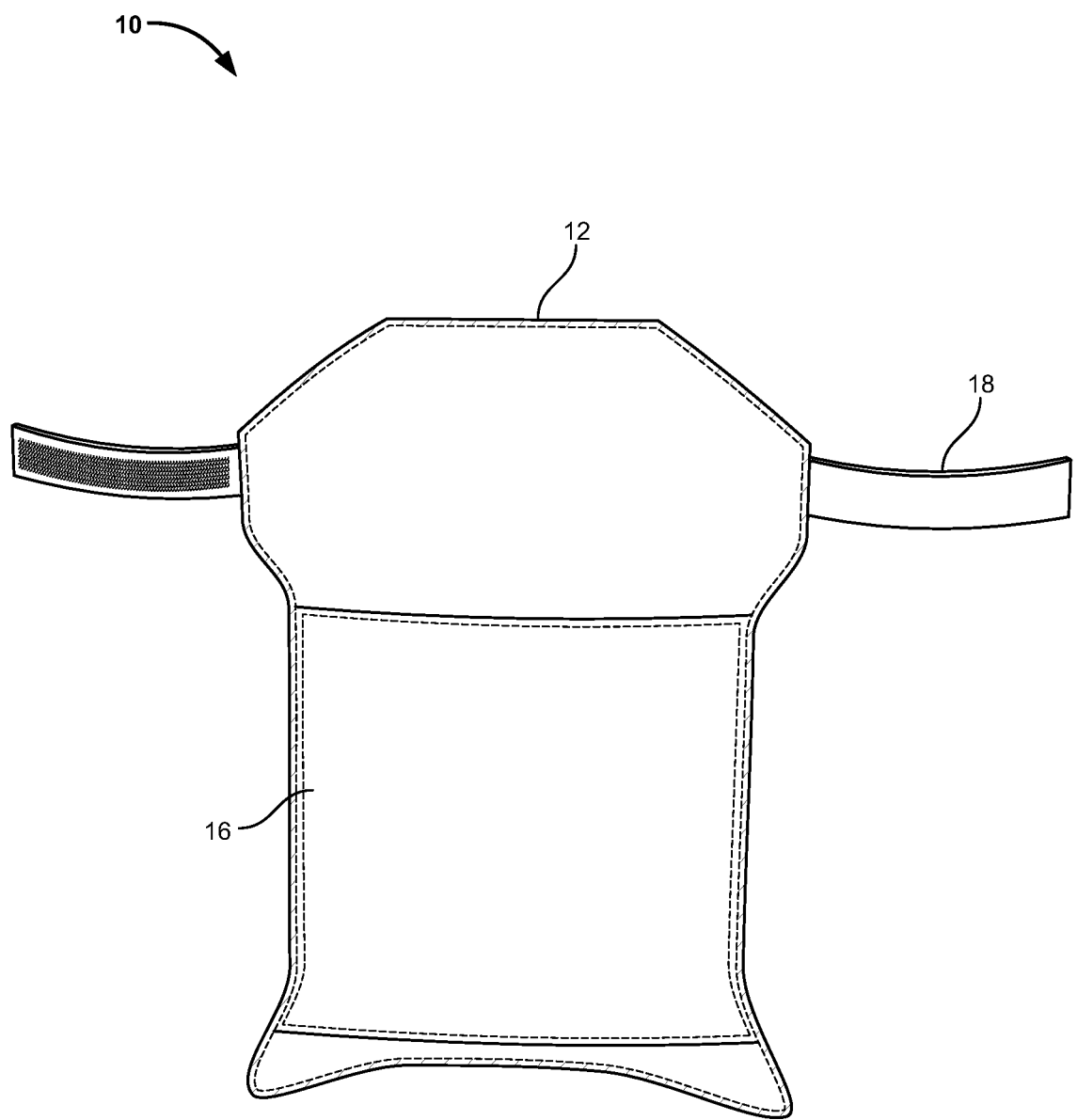
FIG. 3 illustrates a sectional view of the urine bag 10, in accordance with an embodiment of the present invention.

Referring now to FIGS. 1 thru 4, where the present invention is generally referred to with numeral 10, it can be observed that a urine bag 10, in accordance with an embodiment of the present invention, comprises a body 12, a capturing means 14 extending from the body 12, an absorbing means 16 disposed within the body 12, and a strap means 18 provided on the body 12 for allowing the urine bag 10 to be worn by the user.

The body 12 of the urine bag 10 is the containing portion of the urine bag 10. The urine from the user's body is collected within the body in a manner that even accidental leaks or spills are prevented, thereby saving the user from any kind of embarrassment.

The body 12 further comprises the capturing means 14. In accordance with an embodiment of the present invention, the capturing means 14 is a catheter configured to evacuate urine from a bladder of the user. The capturing means 14 has a design that is configured to evacuate the urine from the bladder in a manner that prevents any leakage therefrom.

The body 12 further comprises the absorbing means 16 disposed within the body 12 to receive the bodily fluid and convert the bodily fluid into a gel, thereby preventing the leakage out of the body 12. In one embodiment, the the absorbing means 16 is an absorbent pad made of super absorbent polymers. In an embodiment, the super absorbent polymer is at least one of sodium polyacrylate, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

In accordance with the present invention, the body 12 has a resealable configuration facilitated by a resealing means 20. In an embodiment, the resealing means 20 include a press-fit seal. The resealable configuration allows a user to open the body 12 and replace the absorbing means 16 within the body 12. This allows the bag 10 to reused by the user just by replacing the absorbing means 16 at regular time intervals. In accordance with the present invention, the absorbing means 16 can absorb at least 16 ounces of fluid.

Figure 4:
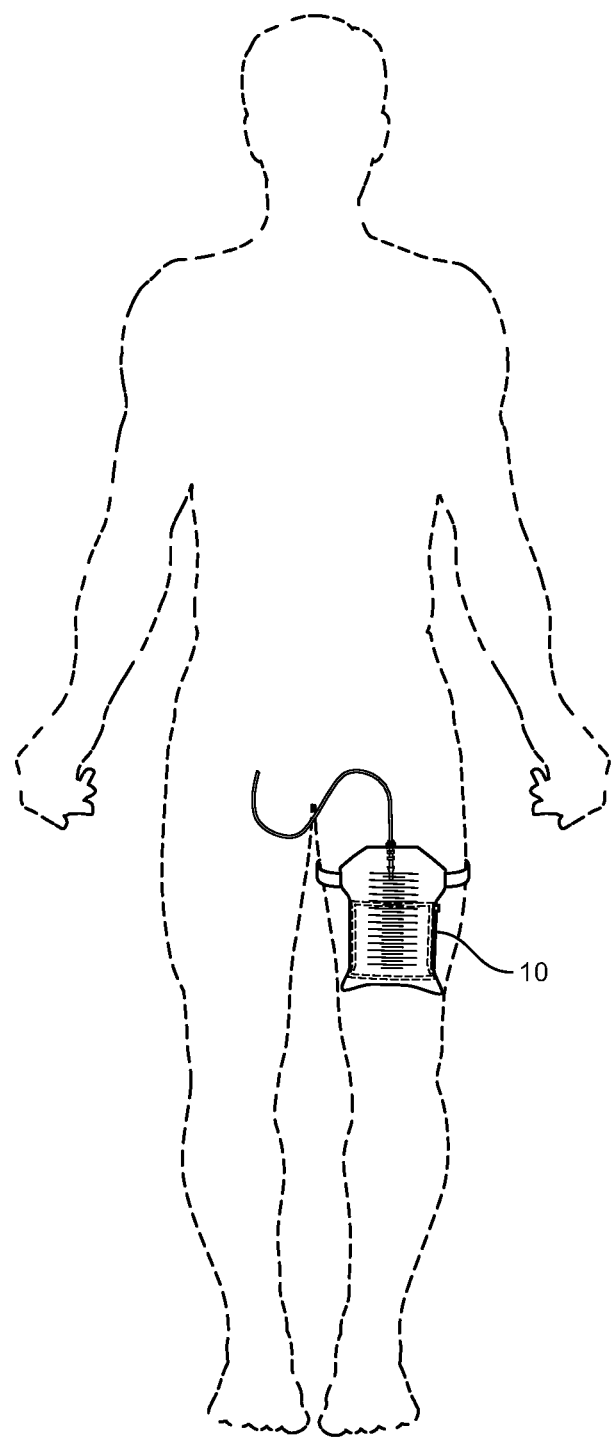
FIG. 4 illustrates a schematic view of the urine bag 10 being worn by a user, in accordance with an embodiment of the present invention.

The bag 10 further comprises the strap means 18 for making the bag wearable on the human body. As seen in FIG. 4, the bag 10 can be worn on the thigh of a user, in one example. Similarly, the bag 10 can also be worn elsewhere on the body.

The bag 10, in accordance with the present invention, has been designed to convert the bodily liquids into gel by the use of absorbing means 16. This causes the conversion of the liquid into gel, thereby eliminating the possibility of accidental spills or leakage from the bag 10. This saves the user from being caught into embarrassing situations caused due to accidental leakage or spillage.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A bag for capturing bodily fluids, the bag comprising:
   a. a body, said body being tapered, said body having a top end and a lower end, said top end being wider than said lower end, said body further including a press fit seal at a lateral edge of said lower end, said body further including straps extending from lateral sides of said top end;
   b. a capturing means coupled to the body for capturing the bodily fluid and allow the bodily fluid to be collected within the body, said capturing means being flexible and partially extending within said top end; and
   c. an absorbing means disposed within the body to receive the bodily fluid and convert the bodily fluid into a gel, thereby preventing the leakage out of the body, said absorbing means being an absorbent pad, said press fit seal being adjacent to said absorbent pad, said absorbent pad being entirely below said straps, said absorbent pad being centrally located within said lower end and expanding entirely within the body, wherein said lower end includes pointed distal ends extending outwardly and away from said lower end, said absorbent pad being entirely above of said pointed distal ends.

2. The bag according to claim 1, wherein the absorbent pad is made of super absorbent polymers.

3. The bag according to claim 2, wherein the super absorbent polymer is at least one of sodium polyacrylate, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

4. The bag according to claim 1, wherein the capturing means is a catheter, and the bodily fluid that the catheter captures is urine.

5. The bag according to claim 1, wherein said body includes markings along a front of said body, said markings alternating in width along a height of said body, said markings being parallel to each other, said markings extending a partial width of said body.

6. The bag according to claim 1, wherein said press fit seal extends a partial height of said lower end and is entirely below said top end.

7. The bag according of claim 1, wherein said top end has a height less than that of said lower end.

8. The bag according to claim 1, wherein said absorbent pad includes four perimeter sides.

9. The bag according to claim 1, wherein said absorbent pad extends within at least half of a space of said lower end.

10. The bag according to claim 1, wherein said absorbent pad has an area which extends substantially within a volume of said lower end.

11. A bag for capturing bodily fluids, the bag consisting of:
   a. a body, said body being tapered, said body having a top end and a lower end, said top end being wider than said lower end, said body further including a press fit seal at a lateral edge of said lower end, said body further including straps extending from lateral sides of said top end, said top end having a height less than that of said bottom end, said press fit seal extending a partial height of said lower end and being entirely below said top end;
   b. a catheter coupled to the body for capturing the bodily fluid and allow the bodily fluid to be collected within the body, said catheter being flexible and partially extending within said top end; and
   c. an absorbent pad disposed within the body to receive the bodily fluid and convert the bodily fluid into a gel, thereby preventing the leakage out of the body, said absorbent pad having four perimeter sides, said press fit seal being adjacent to said absorbent pad, said absorbent pad being entirely below said straps, said absorbent pad being centrally located within said lower end and expanding entirely within the body, said absorbent pad having a height less than that of said absorbent pad, the absorbent pad is made of super absorbent polymers, wherein the super absorbent polymer is at least one of sodium polyacrylate, polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile, wherein said lower end includes pointed distal ends extending outwardly and away from said lower end, said absorbent pad being entirely above of said pointed distal ends.

\* \* \* \* \*